US012394046B2

(12) United States Patent
Matsuda et al.

(10) Patent No.: US 12,394,046 B2
(45) Date of Patent: Aug. 19, 2025

(54) REDUCING A LOAD ON A SUPPORT PROCESS BY EXTRACTING A FRAME FROM A MEDICAL IMAGE WITH A PREDETERMINED RATIO

(71) Applicant: FUJIFILM CORPORATION, Tokyo (JP)

(72) Inventors: Hidenori Matsuda, Kanagawa (JP);
Koji Taninai, Kanagawa (JP);
Kazuhiro Makino, Kanagawa (JP);
Hiromu Hayashi, Kanagawa (JP);
Takeyasu Kobayashi, Kanagawa (JP);
Akihito Bettoyashiki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 438 days.

(21) Appl. No.: 17/744,769

(22) Filed: May 16, 2022

(65) Prior Publication Data

US 2022/0375076 A1 Nov. 24, 2022

(30) Foreign Application Priority Data

May 19, 2021 (JP) ................. 2021-084859

(51) Int. Cl.
*G06T 7/00* (2017.01)
*A61B 6/00* (2024.01)
*G06T 7/20* (2017.01)
*G06V 10/25* (2022.01)
*G06V 20/40* (2022.01)

(52) U.S. Cl.
CPC .......... *G06T 7/0012* (2013.01); *A61B 6/4405* (2013.01); *A61B 6/487* (2013.01);
(Continued)

(58) Field of Classification Search
CPC ............ G06T 7/0012; G06T 7/20; G06T 2207/10016; G06T 2207/10064;
(Continued)

(56) References Cited

U.S. PATENT DOCUMENTS 8,988,529 B2 *  3/2015  Kokubun ............... G06T 7/215
                                                    348/172
2009/0041324 A1  2/2009  Yamagata et al.
(Continued)

FOREIGN PATENT DOCUMENTS

JP    2009-61266 A    3/2009
JP    2011-189082 A   9/2011
(Continued)

OTHER PUBLICATIONS

English language translation of the following: Office action dated Nov. 26, 2024 from the JPO in a Japanese patent application No. 2021-084859 corresponding to the instant patent application. This office action translation is submitted now in order to supplement the understanding of the cited references which are being disclosed in the instant Information Disclosure Statement.
(Continued)

*Primary Examiner* — Christopher Wait
(74) *Attorney, Agent, or Firm* — SOLARIS Intellectual Property Group, PLLC

(57) ABSTRACT

A console of a mobile radiography apparatus includes a CPU that acquires a fluoroscopic image captured by a radiation detector and a visible light image captured by a visible light camera as a moving image related to the capture of the fluoroscopic image of a subject by the mobile radiography apparatus. The CPU extracts a frame to be subjected to a support process, which is a diagnosis support process or an imaging support process, from the moving image. A GPU executes the support process for the extracted frame.

17 Claims, 9 Drawing Sheets

(52) U.S. Cl.
CPC .................. *A61B 6/56* (2013.01); *G06T 7/20* (2013.01); *G06V 10/25* (2022.01); *G06V 20/41* (2022.01); *G06V 20/46* (2022.01); *G06T 2207/10016* (2013.01); *G06T 2207/10064* (2013.01); *G06T 2207/10121* (2013.01); *G06V 2201/03* (2022.01)

(58) Field of Classification Search
CPC ........ G06T 2207/10121; A61B 6/4405; A61B 6/487; A61B 6/56; A61B 6/469; A61B 6/541; A61B 6/4441; G06V 10/25; G06V 20/41; G06V 20/46; G06V 2201/03
See application file for complete search history.

(56) References Cited

U.S. PATENT DOCUMENTS

| | | | |
|---|---|---|---|
| 2010/0225777 A1* | 9/2010 | Makino | H04N 23/63 348/222.1 |
| 2011/0226956 A1 | 9/2011 | Miyamoto | |
| 2017/0325771 A1 | 11/2017 | Tsunomori et al. | |
| 2019/0150871 A1 | 5/2019 | Noji | |
| 2019/0336033 A1* | 11/2019 | Takeshima | A61B 6/4241 |

FOREIGN PATENT DOCUMENTS

| | | |
|---|---|---|
| JP | 2017-202208 A | 11/2017 |
| JP | 2019-92612 A | 6/2019 |
| JP | 2020-39526 A | 3/2020 |

OTHER PUBLICATIONS

English language translation of the following: Office action dated Jun. 24, 2025 from the JPO in a Japanese patent application No. 2021-084859 corresponding to the instant patent application.

* cited by examiner

REDUCING A LOAD ON A SUPPORT PROCESS BY EXTRACTING A FRAME FROM A MEDICAL IMAGE WITH A PREDETERMINED RATIO

CROSS-REFERENCE TO RELATED APPLICATIONS

The present application claims priority under 35 U.S.C. § 119 to Japanese Patent Application No. 2021-084859 filed on May 19, 2021. The above application is hereby expressly incorporated by reference, in its entirety, into the present application.

BACKGROUND

1. Technical Field

The present disclosure relates to an image processing device, a mobile medical imaging apparatus, an image processing method, and an image processing program.

2. Description of the Related Art

A technique is known which executes a support process, such as a diagnosis support process or an imaging support process, for medical images such as radiographic images. For example, JP2009-61266A discloses a technique that extracts a partial region including an anatomical part, which is to be subjected to image diagnosis, in a medical image as an image to be subjected to a diagnosis support process in an image diagnosis support processing device.

SUMMARY

In the technique according to the related art, since the diagnosis support process is executed for a partial region of one medical image, the load on the diagnosis support process is less than that in a case in which the diagnosis support process is executed for the entire image.

However, in a case in which the image to be subjected to the support process is a moving image, the number of images to be processed is relatively large. As the number of images to be processed becomes larger, the load on the support process becomes larger. As described above, in a case in which the image to be subjected to the support process is a moving image, the technique according to the related art may not be sufficient to reduce the load on the support process.

The present disclosure has been made in view of the above circumstances, and an object of the present disclosure is to provide an image processing device, a mobile medical imaging apparatus, an image processing method, and an image processing program that can reduce a load on a support process which is a diagnosis support process or an imaging support process.

In order to achieve the above object, according to a first aspect of the present disclosure, there is provided an image processing device comprising at least one processor. The processor acquires a moving image related to capture of a medical image of a subject by a medical imaging apparatus, extracts a frame to be subjected to a support process, which is a diagnosis support process or an imaging support process, from the moving image, and executes the support process for the extracted frame.

According to a second aspect of the present disclosure, in the image processing device according to the first aspect, a condition for starting the support process may be predetermined, and the processor may detect a time when the support process is started on the basis of the condition and extract a frame corresponding to the detected time as a frame, for which the support process is started, from the moving image.

According to a third aspect of the present disclosure, in the image processing device according to the second aspect, the processor may detect the time when the support process is started using the acquired moving image.

According to a fourth aspect of the present disclosure, in the image processing device according to the second aspect or the third aspect, the processor may detect the time when the support process is started on the basis of a movement of the subject in the moving image.

According to a fifth aspect of the present disclosure, in the image processing device according to the second aspect or the third aspect, the processor may detect the time when the support process is started on the basis of a detection result of an ecological information detection sensor that detects ecological information of the subject.

According to a sixth aspect of the present disclosure, in the image processing device according to the second aspect, the processor may detect the time when the support process is started according to a time when an instruction to execute the support process is received.

According to a seventh aspect of the present disclosure, in the image processing device according to the first aspect, the processor may extract the frame to be subjected to the support process at a regular interval from the moving image.

According to an eighth aspect of the present disclosure, in the image processing device according to any one of the first to seventh aspects, the processor may specify a region of interest from the frame to be subjected to the support process and execute the support process for the region of interest in the frame.

According to a ninth aspect of the present disclosure, in the image processing device according to the eighth aspect, the medical imaging apparatus may be a radiography apparatus that captures a radiographic image, and the moving image is a fluoroscopic image. The processor may specify the region of interest on the basis of an irradiation field of radiation in the radiography apparatus.

In order to achieve the above object, according to a tenth aspect of the present disclosure, there is provided an image processing device comprising at least one processor. The processor acquires a frame to be subjected to a support process, which is a diagnosis support process or an imaging support process, from a moving image related to capture of a medical image of a subject by a medical imaging apparatus and executes the support process for the extracted frame.

According to an eleventh aspect of the present disclosure, in the image processing device according to any one of the first to tenth aspects, the medical imaging apparatus may be a radiography apparatus that captures a radiographic image, and the moving image may be a fluoroscopic image of the subject captured by the radiography apparatus.

According to a twelfth aspect of the present disclosure, in the image processing device according to any one of the first to tenth aspects, the moving image may be a visible light image captured by a visible light imaging device.

In order to achieve the above object, according to a thirteenth aspect of the present disclosure, there is provided a mobile medical imaging apparatus comprising: the image processing device according to the present disclosure; and a power source that supplies power to the processor of the image processing device.

Further, in order to achieve the above object, according to a fourteenth aspect of the present disclosure, there is provided an image processing method that is executed by a computer. The image processing method comprises: acquiring a moving image related to capture of a medical image of a subject by a medical imaging apparatus; extracting a frame to be subjected to a support process, which is a diagnosis support process or an imaging support process, from the moving image; and executing the support process for the extracted frame.

Furthermore, in order to achieve the above object, according to a fifteenth aspect of the present disclosure, there is provided an image processing method that is executed by a computer. The image processing method comprises: acquiring a frame to be subjected to a support process, which is a diagnosis support process or an imaging support process, from a moving image related to capture of a medical image of a subject by a medical imaging apparatus; and executing the support process for the extracted frame.

Moreover, in order to achieve the above object, according to a sixteenth aspect of the present disclosure, there is provided an image processing program that causes a computer to execute a process comprising: acquiring a moving image related to capture of a medical image of a subject by a medical imaging apparatus; extracting a frame to be subjected to a support process, which is a diagnosis support process or an imaging support process, from the moving image; and executing the support process for the extracted frame.

Further, in order to achieve the above object, according to a seventeenth aspect of the present disclosure, there is provided an image processing program that causes a computer to execute a process comprising: acquiring a frame to be subjected to a support process, which is a diagnosis support process or an imaging support process, from a moving image related to capture of a medical image of a subject by a medical imaging apparatus; and executing the support process for the extracted frame.

According to the present disclosure, it is possible to reduce the load on the support process, which is the diagnosis support process or the imaging support process.

BRIEF DESCRIPTION OF THE DRAWINGS

Exemplary embodiments according to the technique of the present disclosure will be described in detail based on the following figures, wherein.

DETAILED DESCRIPTION

Hereinafter, an embodiment of the present disclosure will be described in detail with reference to the drawings. In the following embodiment, an aspect will be described in which a radiographic image is applied as an example of a medical image according to the present disclosure and a mobile radiography apparatus comprising a C-arm is applied as an example of a mobile medical imaging apparatus according to the present disclosure. In addition, this embodiment does not limit the present disclosure.

Figure 1:
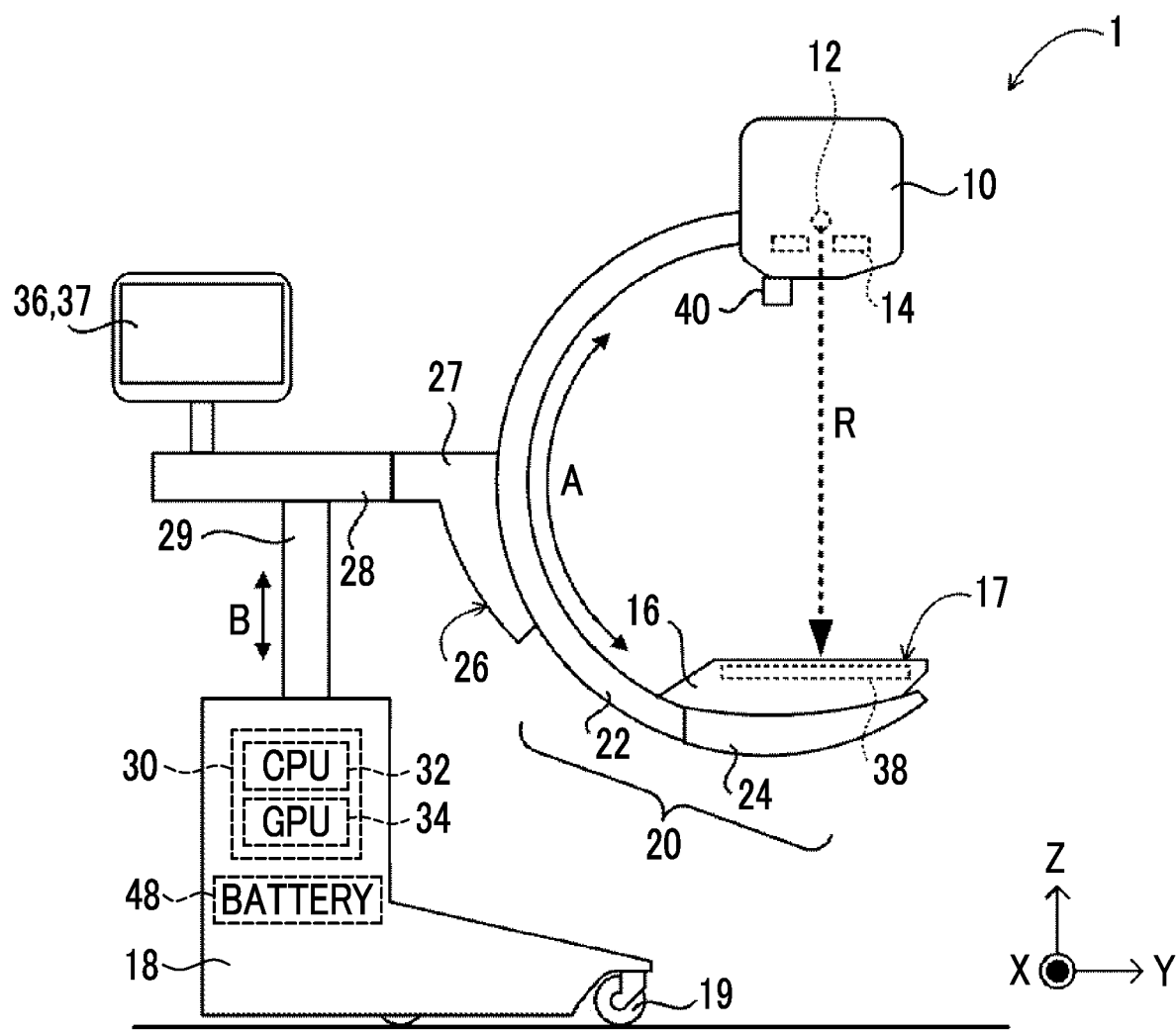
FIG. 1 is a diagram illustrating an example of the overall configuration of a mobile radiography apparatus according to an embodiment.

First, an example of the overall configuration of the mobile radiography apparatus according to this embodiment will be described. FIG. 1 is a diagram illustrating an example of the overall configuration of a mobile radiography apparatus 1 according to this embodiment.

As illustrated in FIG. 1, the mobile radiography apparatus 1 according to this embodiment comprises a C-arm 20 having an arm portion 22 and a holding portion 24. A radiation emitting unit 10 that emits radiation R generated by a radiation source 12 is provided at one end of the arm portion 22.

The radiation source 12 and an irradiation field limiter 14 are accommodated in the radiation emitting unit 10. The radiation source 12 has a radiation tube (not illustrated) that generates the radiation R and has a function of emitting the radiation R generated by the radiation tube. The irradiation field limiter 14 is a so-called collimator that has a function of limiting the irradiation field of the radiation R generated by the radiation tube. For example, the irradiation field limiter 14 has a configuration in which four shielding plates made of lead or the like that shields the radiation R are disposed on each side of a quadrangle and a quadrangular opening portion for transmitting the radiation R is formed in a central portion. The irradiation field limiter 14 changes the position of each shielding plate to change the size of the opening portion, thereby changing the irradiation field of the radiation R.

Further, as illustrated in FIG. 1, a visible light camera 40 is provided on the side where the radiation R is emitted from the radiation emitting unit 10, that is, on the side facing a radiation detector 38. The visible light camera 40 is a visible light imaging device that captures a visible light image. In this embodiment, the visible light camera 40 can capture at least a moving image. Specifically, the visible light camera 40 has a function of capturing a still image at a predetermined interval and sequentially outputting image data indicating the captured still image as a moving image. In addition, in this embodiment, the "moving image" means a set of still images that are continuous in time. Further, in this embodiment, one frame of a still image that is the source of the moving image is referred to as a "frame". In the following description, in a case in which the visible light image captured by the visible light camera 40 is not referred to as a still image or a moving image, it means a moving image.

In this embodiment, the visible light image captured by the visible light camera 40 is used by an operator to check the positioning of a subject. Therefore, a range required for checking the positioning of the subject whose image is to be captured by the radiation detector 38 is an imaging range of the visible light camera 40.

On the other hand, the holding portion 24 is provided at the other end of the arm portion 22. The holding portion 24 holds an accommodation portion 16. The accommodation portion 16 accommodates the radiation detector 38 that detects the radiation R and generates image data indicating a radiographic image. The C-arm 20 according to this embodiment has a function of changing the angle of the radiation detector 38 with respect to the Z direction (vertical direction) illustrated in FIG. 1.

The radiation detector 38 detects the radiation R transmitted through the subject. Specifically, the radiation detector 38 detects the radiation R that has entered the accommodation portion 16 and reached a detection surface of the radiation detector 38, generates a radiographic image on the basis of the detected radiation R, and outputs image data indicating the generated radiographic image. In the following description, in some cases, a series of operations of emitting the radiation R from the radiation source 12 and generating a radiographic image using the radiation detector 38 is referred to as "imaging". The type of the radiation detector 38 according to this embodiment is not particularly limited. For example, the radiation detector 38 may be an indirect-conversion-type radiation detector that converts the radiation R into light and converts the converted light into charge or a direct-conversion-type radiation detector that directly converts the radiation R into charge. Further, in this embodiment, the radiation detector 38 can capture a radiographic image that is at least a moving image of a still image and a moving image. In addition, the radiographic image captured as a moving image is also called a fluoroscopic image.

An imaging surface 17 irradiated with the radiation R emitted from the radiation emitting unit 10 is provided on a side of the accommodation portion 16 which faces the radiation emitting unit 10. In addition, in the mobile radiography apparatus 1 according to this embodiment, a so-called source to image distance (SID) which is a distance between the imaging surface 17 and the radiation source 12 of the radiation emitting unit 10 is a fixed value.

The C-arm 20 is held by a C-arm holding portion 26 so as to be movable in the direction of an arrow A illustrated in FIG. 1. Further, the C-arm holding portion 26 has a shaft portion 27, and the shaft portion 27 connects the C-arm 20 to a bearing 28. The C-arm 20 is rotatable about the shaft portion 27 as a rotation axis.

Furthermore, as illustrated in FIG. 1, the mobile radiography apparatus 1 according to this embodiment comprises a main body portion 18 that has a plurality of wheels 19 provided at the bottom. A support shaft 29 that is expanded and contracted in the Z-axis direction of FIG. 1 is provided in an upper part of a housing of the main body portion 18 in FIG. 1. The bearing 28 is held in the upper part of the support shaft 29 so as to be movable in the direction of an arrow B.

Further, a display unit 36 and an operation unit 37 are provided in the upper part of the main body portion 18. The display unit 36 and the operation unit 37 function as a user interface. The display unit 36 provides an operator, such as a technician or a doctor, who takes a radiographic image with the mobile radiography apparatus 1 with the captured radiographic image or information related to the capture of the radiographic image. The display unit 36 is not particularly limited. Examples of the display unit 36 include a liquid crystal monitor and a light emission diode (LED) monitor. In addition, in this embodiment, a touch panel display integrated with the operation unit 37 is applied as an example of the display unit 36. Further, the operator operates the operation unit 37 to input an instruction related to the capture of a radiographic image. The operation unit 37 is not particularly limited. Examples of the operation unit 37 include various switches, a touch panel, a touch pen, and a mouse. Furthermore, a plurality of operation units 37 may be provided. For example, a touch panel and a foot switch operated by the operator with his or her feet may be provided as the operation unit 37.

Moreover, the main body portion 18 accommodates, for example, a central processing unit (CPU) 32 and a graphics processing unit (GPU) 34 of a console 30 and a battery 48 that supplies power to each unit of the mobile radiography apparatus 1.

Figure 2:
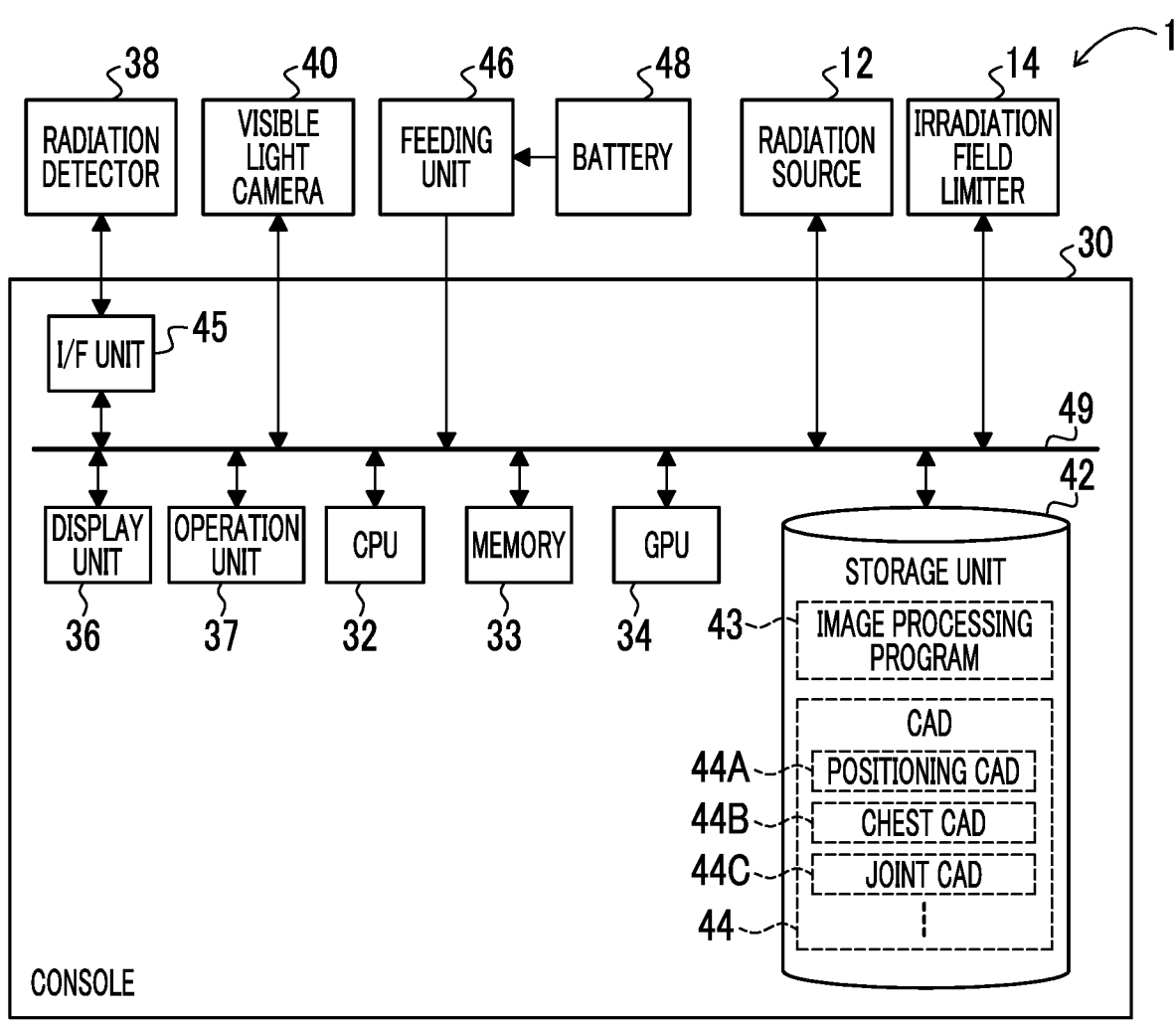
FIG. 2 is a block diagram illustrating an example of the configuration of the mobile radiography apparatus according to the embodiment.

FIG. 2 is a block diagram illustrating an example of the configuration of the mobile radiography apparatus 1 according to this embodiment. As illustrated in FIG. 2, the mobile radiography apparatus 1 according to this embodiment comprises the radiation source 12, the irradiation field limiter 14, the console 30, the radiation detector 38, the visible light camera 40, a feeding unit 46, and the battery 48.

The console 30 has a function of performing control related to the capture of a radiographic image by the mobile radiography apparatus 1. The console 30 according to this embodiment is an example of an image processing device according to the present disclosure.

The console 30 comprises the CPU 32, a memory 33, the GPU 34, the display unit 36, the operation unit 37, a storage unit 42, and an I/F unit 45. The CPU 32, the memory 33, the GPU 34, the display unit 36, the operation unit 37, the storage unit 42, and the I/F unit 45 are connected to each other through a bus 49, such as a system bus or a control bus, such that they can transmit and receive various kinds of information. In addition, the radiation source 12, the irradiation field limiter 14, the visible light camera 40, and the feeding unit 46 are also connected to the bus 49.

The CPU 32 reads out various programs including an image processing program 43 stored in the storage unit 42 to the memory 33 and executes a process corresponding to the read-out program. Therefore, the CPU 32 controls the operation of each unit of the mobile radiography apparatus 1. The CPU 32 according to this embodiment is an example of a processor according to the present disclosure. The memory 33 is a work memory that is used by the CPU 32 to perform processes. The GPU 34 has a function of applying a computer-assisted detection/diagnosis (CAD) 44 stored in the storage unit 42 to execute a support process that is a diagnosis support process or an imaging support process, which will be described in detail below, under the control of the CPU 32.

The storage unit 42 stores, for example, the image processing program 43, the CAD 44 which is an algorithm applied to the support process, the image data of the radiographic image captured by the radiation detector 38, and various other kinds of information. The CAD 44 includes various algorithms corresponding to the types of support processes which will be described below. For example, the CAD 44 according to this embodiment includes a positioning CAD 44A that is applied to the imaging support process for supporting positioning. In addition, the CAD 44 includes, for example, a chest CAD 44B and a joint CAD 44C which are applied to the diagnosis support process for supporting the interpretation of a fluoroscopic image. In addition, the algorithms included in the CAD 44 are not limited thereto. A specific example of the storage unit 42 is a hard disk drive (HDD), a solid state drive (SSD), or the like.

The I/F unit 45 transmits and receives various kinds of information to and from the radiation detector 38 using wireless communication or wired communication. Further, the I/F unit 45 transmits and receives various kinds of information to and from an external device through a network using wireless communication or wired communication. Examples of the external device include a radiology information system (RIS) that manages an imaging order and a picture archiving and communication system (PACS).

Furthermore, as described above, the feeding unit 46 is connected to the bus 49. The feeding unit 46 supplies power from the battery 48 to each unit of the mobile radiography apparatus 1. The feeding unit 46 includes, for example, a direct current (DC)-DC converter that converts a direct current voltage from the battery 48 into a voltage having a value corresponding to a supply destination and a voltage stabilizing circuit that stabilizes the value of the converted voltage. The battery 48 according to this embodiment is provided in the main body portion 18 as described above. As described above, the mobile radiography apparatus 1 is wirelessly driven by the battery 48. In addition, a power cord plug (not illustrated) that extends from the bottom of the main body portion 18 in the mobile radiography apparatus 1 can be inserted into an outlet of a commercial power supply to charge the battery 48, or the mobile radiography apparatus 1 can be operated by power from the commercial power supply.

Further, the console 30 according to this embodiment has a function of executing the support process, which will be described in detail below, for a frame to be subjected to the support process in each of the fluoroscopic images captured by the radiation detector 38 and the visible light images captured by the visible light camera 40. For example, the console 30 according to this embodiment has a function of executing the support process for the moving image related to the capture of the radiographic image of the subject by the mobile radiography apparatus 1. For example, in this embodiment, the console 30 has a function of executing the support process for each of the visible light image of the subject captured by the visible light camera 40 in the capture of the radiographic image of the subject by the mobile radiography apparatus 1 and the radiographic image captured by the radiation detector 38 in the capture of the radiographic image by the mobile radiography apparatus 1.

In other words, the console 30 has a function of executing the imaging support process for supporting the positioning of the subject for the frame to be processed which has been extracted from the visible light images captured by the visible light camera 40. Further, the console 30 has a function of executing the diagnosis support process for supporting the interpretation of the fluoroscopic image for the frame to be processed which has been extracted from the fluoroscopic images captured by the radiation detector 38. In the following description, in a case in which the fluoroscopic image captured by the radiation detector 38 and the visible light image captured by the visible light camera 40 are generically referred to without being distinguished from each other, they are simply referred to as "moving images".

In addition, in this embodiment, each of the fluoroscopic image captured by the radiation detector 38 and the visible light image captured by the visible light camera 40 is an example of a moving image related to the capture of the medical image of the subject by the medical imaging apparatus according to the present disclosure.

Figure 3:
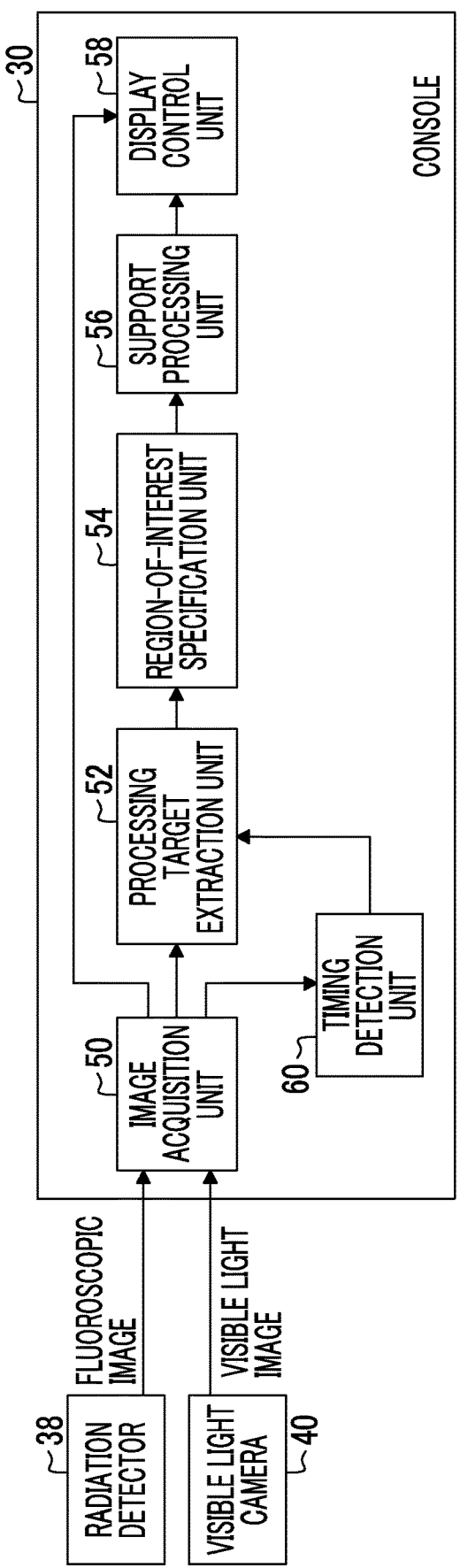
FIG. 3 is a functional block diagram illustrating an example of a configuration related to a function for executing a diagnosis support process in a console according to the embodiment.

FIG. 3 is a functional block diagram illustrating an example of a configuration related to the function of executing the support process in the console 30 according to this embodiment. As illustrated in FIG. 3, the console 30 comprises an image acquisition unit 50, a processing target extraction unit 52, a region-of-interest specification unit 54, a support processing unit 56, a display control unit 58, and a timing detection unit 60. For example, in the console 30 according to this embodiment, the CPU 32 executes the image processing program 43 stored in the storage unit 42 such that the CPU 32 functions as the image acquisition unit 50, the processing target extraction unit 52, the region-of-interest specification unit 54, and the display control unit 58, and the timing detection unit 60 and the GPU 34 functions as the support processing unit 56.

The image acquisition unit 50 has a function of acquiring the moving image related to the capture of the radiographic image of the subject by the mobile radiography apparatus 1. Specifically, as described above, the image acquisition unit 50 according to this embodiment has a function of acquiring the visible light image captured by the visible light camera 40. More specifically, in a case in which an instruction to capture a radiographic image corresponding to an imaging order is input to the mobile radiography apparatus 1, the image acquisition unit 50 sequentially acquires image data indicating the visible light image captured by the visible light camera 40 from the visible light camera 40. In addition, the image acquisition unit 50 according to this embodiment has a function of acquiring the fluoroscopic image captured by the radiation detector 38. More specifically, in a case in which the radiation detector 38 starts to capture a fluoroscopic image, the image acquisition unit 50 sequentially acquires image data indicating the fluoroscopic image captured by the radiation detector 38 from the radiation detector 38. The image acquisition unit 50 outputs the acquired image data indicating the moving image to the processing target extraction unit 52, the display control unit 58, and the timing detection unit 60.

The timing detection unit 60 has a function of detecting the time when the support process is started on the basis of predetermined conditions. In this embodiment, the conditions for starting the support process are predetermined. In a case in which the imaging support process for supporting positioning is executed, an example of the predetermined condition is that a support process execution instruction input by the operator through the operation unit 37 has been received. Therefore, in a case in which the imaging support process for supporting positioning is executed and the support process execution instruction is received, the timing detection unit 60 detects the time when the support process is started and outputs a start signal for starting the support process to the processing target extraction unit 52.

In addition, in a case in which the diagnosis support process for supporting the interpretation of the fluoroscopic image is executed, an example of the predetermined condition is that the support process execution instruction input by the operator through the operation unit 37 has been received or that the subject has made a predetermined movement. Therefore, in a case in which the diagnosis support process for supporting the interpretation of the fluoroscopic image is executed and the support process execution instruction is received or a predetermined movement of the subject is detected, the timing detection unit 60 detects the time when the support process is started and outputs the start signal for starting the support process to the processing target extraction unit 52. In addition, the conditions for starting the support process are not limited to the conditions described in this embodiment. Further, the operator may set the conditions for starting the support process.

The processing target extraction unit 52 has a function of extracting the frame to be subjected to the support process from the moving image input from the image acquisition unit 50. In addition, the processing target extraction unit 52 according to this embodiment extracts a frame corresponding to the start signal input from the timing detection unit 60 as the frame, for which the support process is started, from the moving image. The extraction of the frame, which is a specific object to be processed, by the processing target extraction unit 52 according to this embodiment will be described in detail below. The processing target extraction unit 52 outputs image data indicating the extracted frame to the region-of-interest specification unit 54.

The region-of-interest specification unit 54 has a function of specifying the region of interest from the frame to be subjected to the support process. The region of interest is a region in which the operator is interested in each frame and is a region to be subjected to the support process. Examples of the region in which the operator is interested include a region including a part to be checked at the time of positioning and a region to be interpreted. For example, the region of interest in this embodiment is a region irradiated with the radiation R from the radiation source 12, specifically, a region of the irradiation field of the radiation R limited by the irradiation field limiter 14. Therefore, the region-of-interest specification unit 54 according to this embodiment acquires information indicating the range of the irradiation field of the radiation R from the irradiation field limiter 14 and specifies the region of interest in each frame on the basis of the acquired information. The region-of-interest specification unit 54 outputs information indicating the region of interest specified in each frame to be subjected to the support process to the support processing unit 56.

In addition, as described above, in this embodiment, the region of interest is the region of the irradiation field. However, the region of interest is not limited to this embodiment. For example, the region of interest may be predetermined according to the type of support process. For example, in a case in which the imaging support process for supporting positioning is executed, the region of interest may be a region to be checked by the operator at the time of positioning, depending on the part to be imaged, an imaging method, or the like. Further, for example, in a case in which the diagnosis support process for supporting the interpretation of the fluoroscopic image is executed, the region of interest may be a region interpreted by the operator depending on the part to be treated or imaged. The information indicating the region of interest may be stored in the storage unit 42 so as to be associated with the type of support process, the part to be imaged, or the like or may be acquired from an external device or the like.

Further, a part at which the operator gazes may be applied as the region of interest. In this case, for example, the region-of-interest specification unit 54 may display the fluoroscopic image acquired from the radiation detector 38 on the display unit 36 and specify the region at which the operator gazes in the fluoroscopic image as the region of interest. Further, for example, a region in which the operator gazes at the subject may be specified as the region of interest. In addition, the aspect in which the region-of-interest specification unit 54 specifies the region at which the operator gazes is not particularly limited. For example, the existing technique can be applied. For example, the following aspect may be applied: the region-of-interest specification unit 54 performs image analysis on a moving image obtained by imaging the face of the operator with the visible light camera 40 or the like to analyze the orientation of the face of the operator, the position of the eyeball, or the like, derives information including the line of sight of the operator and the time during which the line of sight is maintained, and specifies the region at which the operator gazes on the basis of the derived information.

The support processing unit 56 has a function of executing the support process for the region of interest of each frame extracted by the processing target extraction unit 52. Specifically, the support processing unit 56 performs the support process by applying the CAD algorithm selected from the CAD 44 stored in the storage unit 42 according to the type of support process designated by the operator to the region of interest in the frame to be subjected to the diagnosis support process. In addition, the specification of the type of support process by the operator will be described in detail below. The support processing unit 56 outputs the processing result of the support process to the display control unit 58. As described above, the support processing unit 56 according to this embodiment executes the support process for the region of interest which is a partial region of the frame. Therefore, it is possible to reduce the load on the support process, as compared to a case in which the support process is executed for the entire frame.

The display control unit 58 has a function of displaying the processing result of the support processing unit 56 on the display unit 36. The display control unit 58 according to this embodiment also displays, on the display unit 36, a frame other than the frame to be subjected to the support process among the visible light images or the fluoroscopic images acquired by the image acquisition unit 50.

Figure 4:
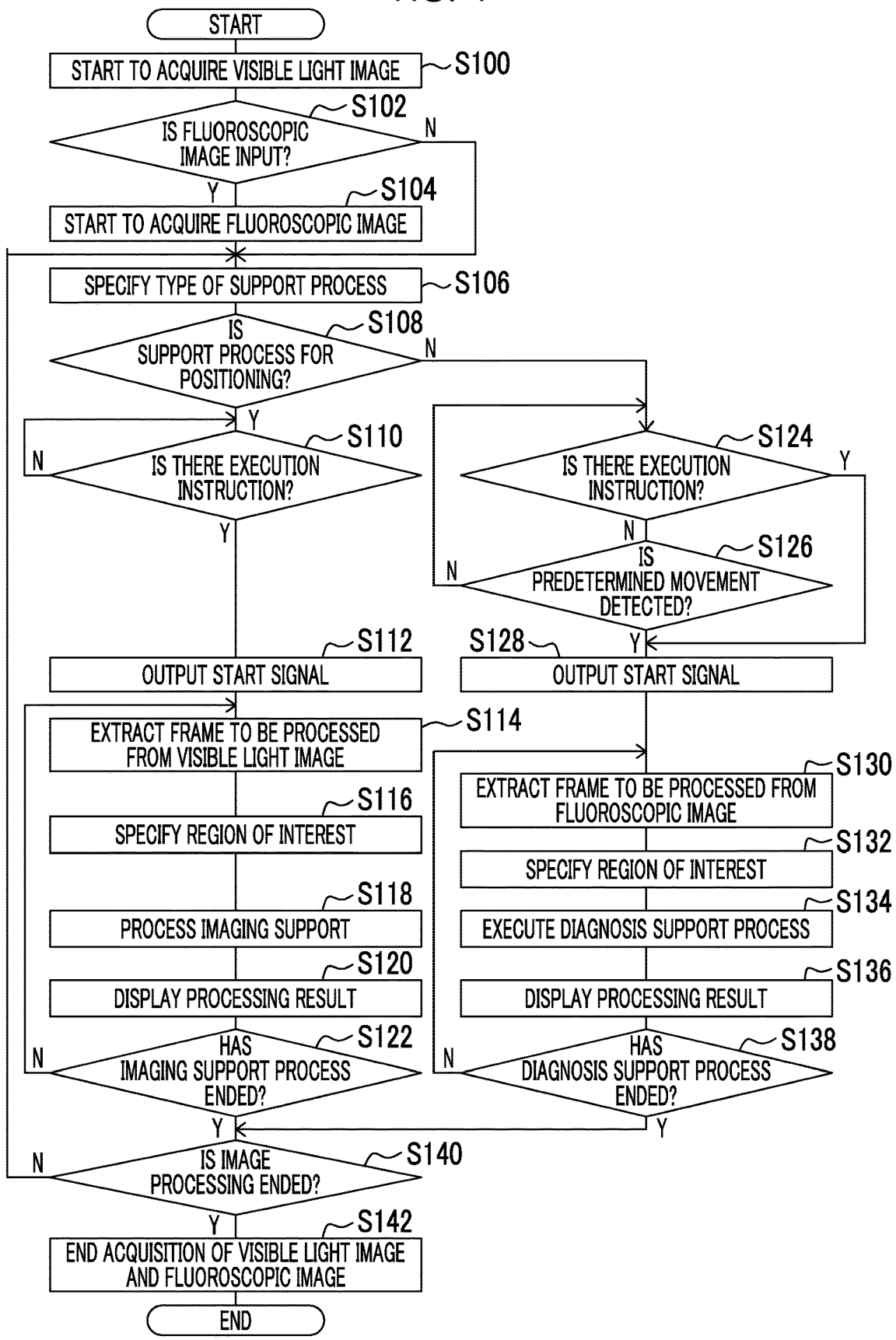
FIG. 4 is a flowchart illustrating an example of the flow of image processing by the console according to the embodiment.

Next, the operation of the console 30 related to the support process will be described with reference to the drawings. In a case in which an instruction to capture a radiographic image corresponding to an imaging order is input, the console 30 according to this embodiment executes image processing illustrated in FIG. 4. FIG. 4 is a flowchart illustrating an example of the flow of the image processing performed by the console 30 according to this embodiment. In the console 30 according to this embodiment, for example, the CPU 32 executes the image processing program 43 stored in the storage unit 42 to perform the image processing whose example is illustrated in FIG. 4.

In Step S100 of FIG. 4, the image acquisition unit 50 starts to acquire the visible light image. As described above, the image acquisition unit 50 according to this embodiment starts to acquire the visible light image captured by the visible light camera 40.

Then, in Step S102, the image acquisition unit 50 determines whether or not a fluoroscopic image has been input from the radiation detector 38. As described above, in a case in which the capture of the fluoroscopic image is started, the radiation detector 38 sequentially outputs the frame constituting the fluoroscopic image to the console 30. Then, the image acquisition unit 50 determines whether or not the frame constituting the fluoroscopic image has been input to the console 30 from the radiation detector 38.

In a case in which the fluoroscopic image has not been input to the console 30, the determination result in Step S102 is "No", and the process proceeds to Step S106. On the other hand, in a case in which the fluoroscopic image has been input to the console 30, the determination result in Step S102 is "Yes", and the process proceeds to Step S104.

In Step S104, the image acquisition unit 50 starts to acquire the fluoroscopic image. As described above, the image acquisition unit 50 according to this embodiment starts to acquire the fluoroscopic image output from the radiation detector 38.

Then, in Step S106, the timing detection unit 60 specifies the type of support process. As described above, in this embodiment, the types of support processes include the imaging support process for supporting positioning and the diagnosis support process for supporting the interpretation of the fluoroscopic image. In addition, there are a plurality of types of imaging support processes and a plurality of types of diagnosis support processes. Examples of the diagnosis support process for supporting the interpretation of the fluoroscopic image include a diagnosis support process for supporting the interpretation of the position and state of a surgical tool or the like in the fluoroscopy image and a diagnosis support process for supporting the interpretation of various lesions. Further, there are types of diagnosis support corresponding to the parts to be imaged and the like. As described above, the type of support process is not particularly limited. For example, a plurality of types of support processes can be provided depending on the operator, the interpreter, the subject, the imaging method, and the like.

For example, the timing detection unit 60 according to this embodiment displays, on the display unit 36, information indicating the type of support process, such as the name of the CAD applied in the support process, receives information indicating the type of support process selected by the operator from the displayed information, and specifies the type of support process. In addition, the method by which the timing detection unit 60 specifies the type of support process is not particularly limited. For example, the type of support process may be associated with the imaging order, and the timing detection unit 60 may specify the type of support process associated with the imaging order.

Then, in Step S108, the timing detection unit 60 determines whether or not the type of support process specified in Step S106 is the imaging support process for supporting positioning. In a case in which the specified type of support process is the imaging support process for supporting positioning, the determination result in Step S108 is "Yes", and the process proceeds to Step S110.

In Step S110, the timing detection unit 60 determines whether or not the support process execution instruction has been received. The determination result in Step S110 is "No" until the support process execution instruction is received. On the other hand, in a case in which the support process execution instruction has been received, the determination result in Step S110 is "Yes", and the process proceeds to Step S112.

In Step S112, the timing detection unit 60 outputs the start signal for starting the support process to the processing target extraction unit 52 as described above. Further, in this embodiment, information indicating that the type of the support process specified in Step S106 is the imaging support process for supporting positioning is also output to the processing target extraction unit 52.

Then, in Step S114, the processing target extraction unit 52 extracts the frame to be subjected to the support process from the visible light image. The processing target extraction unit 52 according to this embodiment extracts the frame to be subjected to the support process from the visible light images at a frame rate determined in the imaging support process for supporting positioning.

Figure 5:
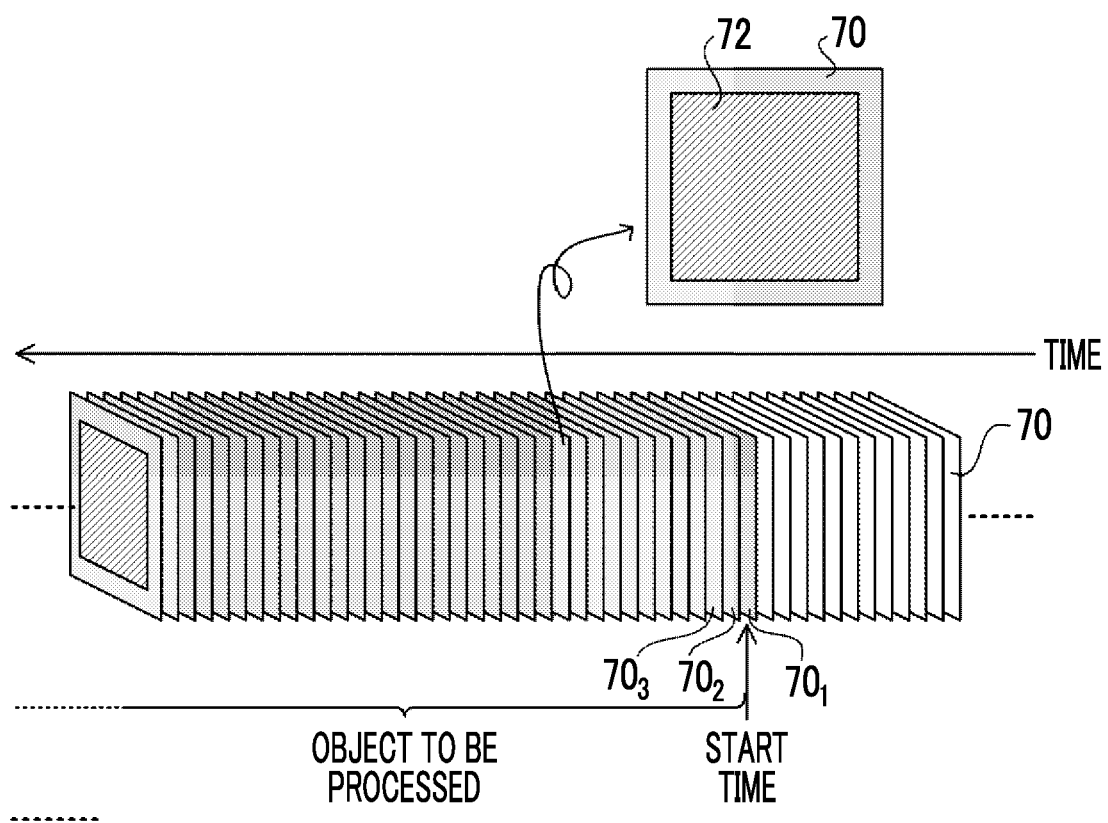
FIG. 5 is a diagram illustrating an object to be subjected to the diagnosis support process in a case in which the diagnosis support process for supporting positioning is executed.

The object to be subjected to the support process in a case in which the imaging support process for supporting positioning is executed will be described with reference to FIG. 5. As described above, in this embodiment, a visible light image 70 that the image acquisition unit 50 has started to acquire in Step S100 is input to the processing target extraction unit 52. In a case in which the processing target extraction unit 52 receives the start signal output by the timing detection unit 60 in Step S112, the processing target extraction unit 52 extracts, as the frames to be processed, frames (702, 703, . . . ) subsequent to a frame 701 corresponding to the start signal among the visible light images 70.

Then, in Step S116, the region-of-interest specification unit 54 specifies a region of interest 72 (see FIG. 5) from the frame to be processed which has been extracted by the processing target extraction unit 52 in Step S114. As described above, the region-of-interest specification unit 54 according to this embodiment specifies a region corresponding to the irradiation field defined by the opening portion of the irradiation field limiter 14 as the region of interest 72 from the frame to be processed.

Then, in Step S118, the support processing unit 56 executes the imaging support process for the region of interest 72 specified in Step S116 from the frame to be processed which has been extracted by the processing target extraction unit 52 in Step S114. Specifically, the support processing unit 56 selects the algorithm of the positioning CAD 44A corresponding to the imaging support process from the CAD 44 stored in the storage unit 42 in order to support positioning. Further, the support processing unit 56 applies the selected algorithm of the positioning CAD 44A to the region of interest 72 in the frame to be subjected to the imaging support process to execute the imaging support process for supporting positioning.

In addition, the details of the positioning CAD 44A are not particularly limited as long as the positioning CAD 44A can provide information for supporting the positioning required in the capture of a fluoroscopic image by the mobile radiography apparatus 1. For example, the positioning CAD 44A may be a CAD for determining whether or not a desired part of the subject is located in the irradiation field. Further, for example, whether the subject lies prone or supine, that is, the orientation of the subject with respect to the radiation detector 38 may be important as positioning. In this case, the positioning CAD 44A may be used as a CAD for determining whether or not the orientation of the subject is appropriate.

Then, in Step S120, the display control unit 58 displays the result of the imaging support process in Step S120 on the display unit 36. In addition, the display mode of the result of the imaging support process by the display control unit 58 is not particularly limited. For example, the display control unit 58 according to this embodiment displays the result of the imaging support process together with the visible light image 70 that has not been subjected to the imaging support process.

Then, in Step S122, the support processing unit 56 determines whether or not to end the imaging support process that is being executed. In a case in which the imaging support process for support positioning is executed, the end condition of the imaging support process is that a support process end instruction input by the operator through the operation unit 37 has been received or that an instruction to emit the radiation R from the operator has been received. In a case in which the end condition is satisfied, the support processing unit 56 determines to end the imaging support process. The determination result in Step S122 is "No" until the end conditions are satisfied, the process returns to Step S114, and the processes in Steps S114 and S118 are repeated. On the other hand, in a case in which the end condition is satisfied, the determination result in Step S122 is "Yes" and the process proceeds to Step S140.

On the other hand, in a case in which the type of support process specified in Step S106 is a support process other than the imaging support process for supporting positioning, the determination result in Step S108 is "No", and the process proceeds to Step S124.

In Step S124, the timing detection unit 60 determines whether or not the support process execution instruction has been received, as in Step S110. On the other hand, in a case in which the support process execution instruction has been received, the determination result in Step S124 is "Yes", and the process proceeds to Step S128. On the other hand, in a case in which the support process execution instruction has not been received, the determination result in Step S124 is "No", and the process proceeds to Step S126.

In Step S126, the timing detection unit 60 determines whether or not a predetermined movement of the subject has been detected. For example, the timing detection unit 60 according to this embodiment detects a predetermined movement of the subject using the visible light image or the fluoroscopic image. In addition, the method by which the timing detection unit 60 detects a predetermined movement of the subject is not particularly limited. For example, in the imaging of the lungs (chest), the imaging time may be determined according to the breathing of the subject. For example, the imaging time is the time when the subject holds breath. In this case, the timing detection unit 60 may detect the movement of the subject corresponding to breathing from the moving image, using image analysis, to detect a predetermined movement. In a case in which the timing detection unit 60 has not detected a predetermined movement, the determination result in Step S126 is "No", and the process returns to Step S124. On the other hand, in a case in which the timing detection unit 60 has detected a predetermined movement, the determination result in Step S126 is "Yes", and the process proceeds to Step S128.

In Step S128, the timing detection unit 60 outputs the start signal for starting the support process to the processing target extraction unit 52 as in Step S112. Further, in this embodiment, information indicating that the type of support process specified in Step S106 is the diagnosis support process for supporting the interpretation of the fluoroscopic image is also output to the processing target extraction unit 52.

Then, in Step S130, the processing target extraction unit 52 extracts the frame to be subjected to the diagnosis support process from the fluoroscopic images. The processing target extraction unit 52 according to this embodiment extracts the frame to be subjected to the diagnosis support process from the fluoroscopic images at a frame rate determined according to the type of diagnosis support process.

Figure 6:
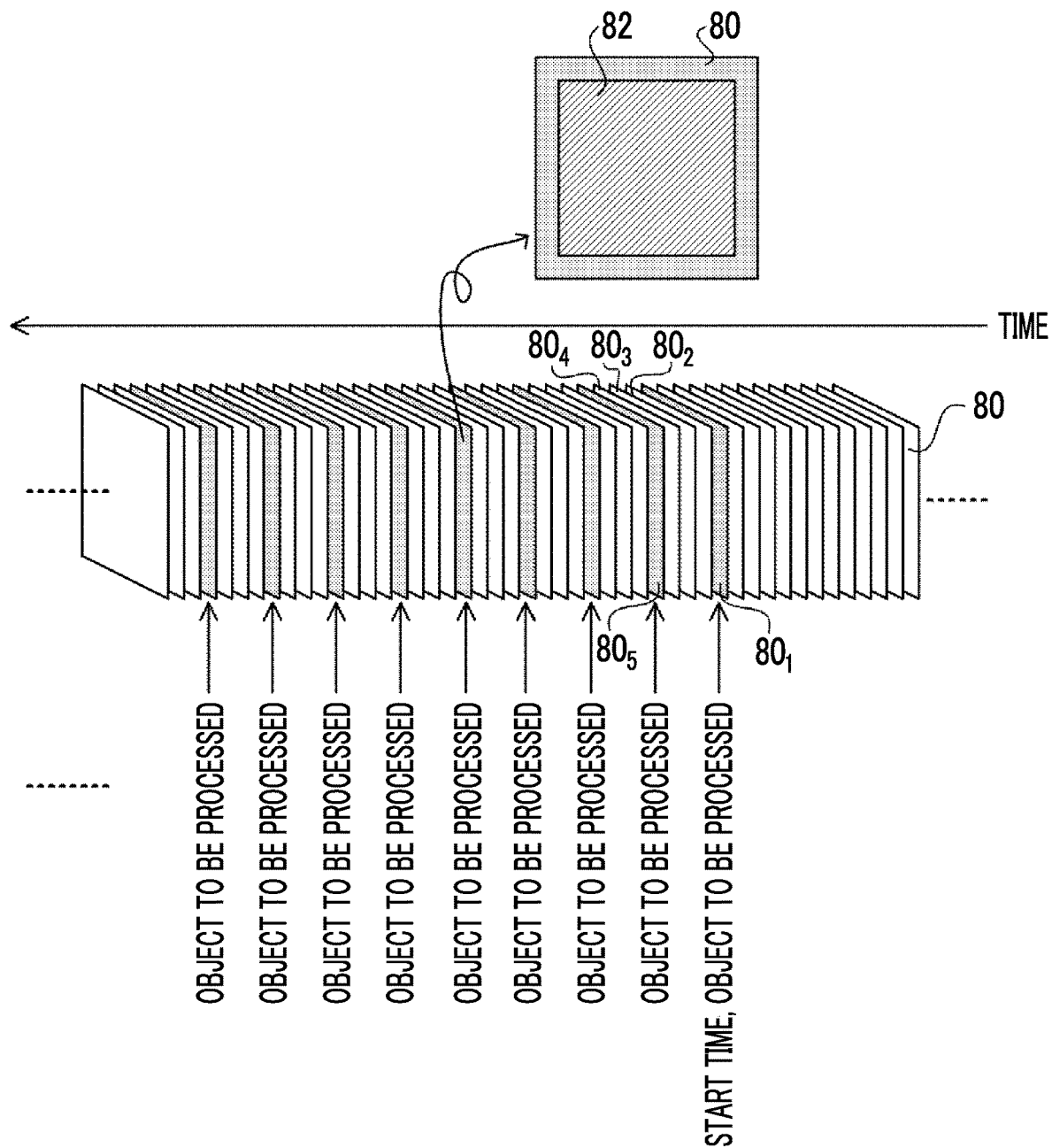
FIG. 6 is a diagram illustrating an object to be subjected to the diagnosis support process in a case in which the diagnosis support process for supporting the interpretation of a fluoroscopic image is executed.

The object to be subjected to the diagnosis support process in a case in which the diagnosis support process for supporting the interpretation of the fluoroscopic image is executed will be described with reference to FIG. 6. As described above, in this embodiment, a fluoroscopic image 80 that the image acquisition unit 50 has started to acquire in Step S104 is input to the processing target extraction unit 52. In a case in which the processing target extraction unit 52 receives the start signal output by the timing detection unit 60 in Step S128, it extracts, as the frames to be processed, frames at regular intervals from frames (802, 803, . . . ) subsequent to a frame 801 corresponding to the start signal among the fluoroscopic images 80. In the example illustrated in FIG. 6, every fourth frame is extracted as the frame to be processed from the fluoroscopic images 80. For example, as illustrated in FIG. 6, the timing detection unit 60 extracts the frame 801 corresponding to the start time as the frame to be processed, does not extract the frames 802 to 804, and extracts the next frame 805 as the frame to be processed.

Then, in Step S132, the region-of-interest specification unit 54 specifies a region of interest 82 (see FIG. 6) from the frame to be processed which has been extracted by the processing target extraction unit 52 in Step S130, as in Step S116. That is, the region-of-interest specification unit 54 specifies a region corresponding to the irradiation field defined by the opening portion of the irradiation field limiter 14 as the region of interest 82 from the frame to be processed.

Then, in Step S134, the support processing unit 56 executes the diagnosis support process for the region of interest 82 specified in Step S132 in the frame to be processed which has been extracted by the processing target extraction unit 52 in Step S130. Specifically, the support processing unit 56 selects a CAD algorithm corresponding to the type of diagnosis support process among the diagnosis support processes for supporting the interpretation of the fluoroscopic image from the CAD 44 stored in the storage unit 42. For example, in a case in which the type of diagnosis support process is a diagnosis support process for the chest, the support processing unit 56 selects the chest CAD 44B from the CAD 44. Further, for example, in a case in which the type of diagnosis support process is a diagnosis support process for a joint, the support processing unit 56 selects the joint CAD 44C from the CAD 44. Furthermore, the support processing unit 56 applies the selected CAD algorithm to the region of interest 82 in the frame to be processed to execute the diagnosis support process for supporting the interpretation of the fluoroscopic image.

In addition, the details of the chest CAD 44B are not particularly limited, and any CAD may be used as long as it supports interpretation required in a case in which the imaging part is the chest. For example, the chest CAD 44B may be at least one of a CAD that specifies the position of the tip of a catheter in a case in which the catheter is inserted or a CAD that specifies a lesion such as pneumothorax or cardiac hypertrophy. Further, the details of the joint CAD 44C are not particularly limited, and any CAD may be used as long as it supports interpretation required in a case in which the imaging part is a joint. For example, the joint CAD 44C may be at least one of a CAD that specifies a fracture or a CAD that specifies the degree of bending of a bone.

Figure 7:
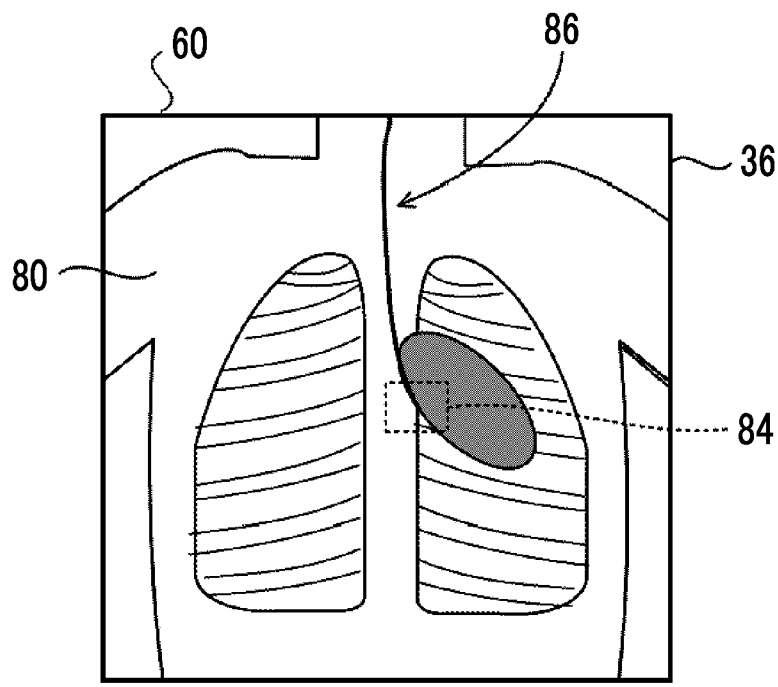
FIG. 7 is a diagram illustrating an example of a display mode in which a display control unit displays a result of the diagnosis support process for supporting the interpretation of the fluoroscopic image on a display unit.

Then, in Step S136, the display control unit 58 displays the result of the diagnosis support process in Step S134 on the display unit 36. In addition, the display mode of the result of the diagnosis support process by the display control unit 58 is not particularly limited. FIG. 7 illustrates an example of a display mode in which the display control unit 58 displays the result of the diagnosis support process for supporting the interpretation of the fluoroscopic image 80 displayed on the display unit 36. FIG. 7 illustrates an example of a display mode in which a result 84 of the diagnosis support process that applies the chest CAD 44B to the fluoroscopic image 80 to specify the position of the tip of a catheter 86.

Then, in Step S138, the support processing unit 56 determines whether or not to end the diagnosis support process that is being executed. In a case in which the diagnosis support process for supporting the interpretation of the fluoroscopic image is executed, the end condition of the diagnosis support process is that a diagnosis support process end instruction input by the operator through the operation unit 37 is received or that the emission of the radiation R is stopped. In a case in which the end condition is satisfied, the support processing unit 56 determines to end the diagnosis support process. The determination result in Step S138 is "No" until the end conditions are satisfied, the process returns to Step S130, and the processes in Steps S130 and S134 are repeated. On the other hand, in a case in which the end condition is satisfied, the determination result in Step S138 is "Yes", and the process proceeds to Step S140.

In Step S140, the image acquisition unit 50 determines whether or not to end the image processing illustrated in FIG. 4. In this embodiment, the end condition of the image processing is that the capture of the fluoroscopic image by the mobile radiography apparatus 1 ends. The determination result of the image acquisition unit 50 in Step S140 is "No" until the end conditions are satisfied, the process returns to Step S106, and the processes in Steps S106 and S138 are repeated. On the other hand, in a case in which the end condition is satisfied, the determination result in Step S140 is "Yes", and the process proceeds to Step S142.

In Step S142, the image acquisition unit 50 ends the acquisition of the visible light image and the fluoroscopic image. As described above, the image acquisition unit 50 according to this embodiment ends the acquisition of the visible light image captured by the visible light camera 40 and the acquisition of the fluoroscopic image captured by the radiation detector 38. In a case in which the process in Step S142 ends, the image processing illustrated in FIG. 4 ends.

As described above, in the console 30 of the mobile radiography apparatus 1 according to the above-described embodiment, the CPU 32 acquires the fluoroscopic image captured by the radiation detector 38 and the visible light image captured by the visible light camera 40 as a moving image related to the capture of the fluoroscopic image of the subject by the mobile radiography apparatus 1. The CPU 32 extracts the frame to be subjected to the support process, which is the diagnosis support process or the imaging support process, from the moving image. The GPU 34 performs the support process for the extracted frame.

As described above, in the console 30 according to the above-described embodiment, the support process is not executed for all the acquired moving image, but is executed for the frame extracted as the object to be processed. Therefore, it is possible to reduce the number of frames to be subjected to the diagnosis support process. As a result, it is possible to reduce the load on the support process which is the diagnosis support process or the imaging support process.

Figure 8:
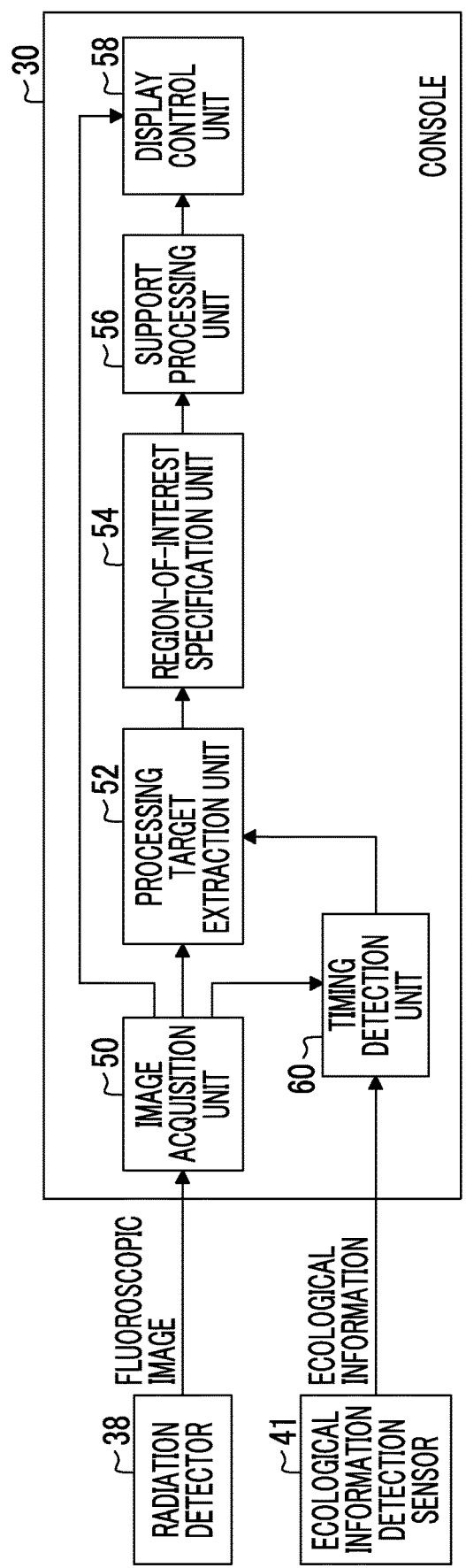
FIG. 8 is a functional block diagram illustrating another example of the configuration related to the function of executing the diagnosis support process in the console according to the embodiment.

Further, in the above-described embodiment, the aspect in which the timing detection unit 60 detects the time when the support process is started on the basis of a predetermined condition, using the moving image acquired by the image acquisition unit 50. However, the timing detection unit 60 may detect the time when the support process is started on the basis of a predetermined condition, using information other than the moving image. For example, the timing detection unit 60 may detect the movement of the subject from information other than the moving image acquired by the image acquisition unit 50. For example, in this case, as illustrated in FIG. 8, the mobile radiography apparatus 1 may comprise an ecological information detection sensor 41, and the timing detection unit 60 may detect the time when the support process is started on the basis of a predetermined condition, using the ecological information of the subject detected by the ecological information detection sensor 41. Examples of the ecological information detection sensor 41 include a motion sensor and a measurement device for measuring expiration or inspiration.

Figure 9:
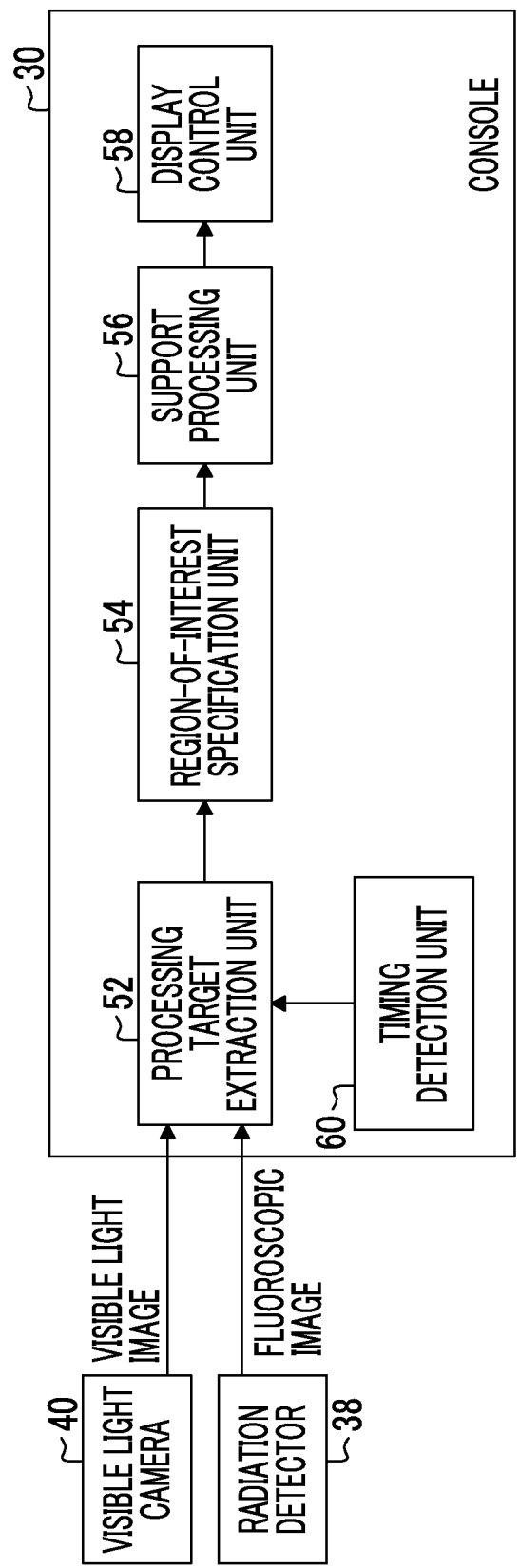
FIG. 9 is a functional block diagram illustrating still another example of the configuration related to the function of executing the diagnosis support process in the console according to the embodiment.

Further, in the above-described embodiment, the aspect in which the processing target extraction unit 52 extracts the frame to be subjected to the support process from the moving image acquired by the image acquisition unit 50 has been described. However, the aspect in which the processing target extraction unit 52 extracts the frame to be subjected to the support process is not limited to this embodiment. As illustrated in FIG. 9, the processing target extraction unit 52 may acquire a frame of a moving image corresponding to the start signal input from the timing detection unit 60 from fluoroscopic image captured by the radiation detector 38 or the visible light image captured by the visible light camera 40 to extract the frame to be subjected to the support process. In other words, the console 30 may acquire the frame to be subjected to the support process, which is the diagnosis support process or the imaging support process, from the moving image related to the capture of the medical image of the subject by the mobile radiography apparatus 1 and execute the support process for the acquired frame.

Further, in the above-described embodiment, the aspect in which the support processing unit 56 applies the CAD algorithm to execute the support process has been described. However, the aspect in which the support process is executed or the CAD is not limited to this embodiment. For example, the support processing unit 56 may apply artificial intelligence (AI) technology to execute the support process or may apply a trained model, which has been machine-trained by deep learning or the like, to execute the support process.

Further, in the above-described embodiment, the aspect in which the console 30 is an example of the image processing device according to the present disclosure has been described. However, devices other than the console 30 may have the functions of the image processing device according to the present disclosure. In other words, a device other than the console 30 may comprise some or all of the image acquisition unit 50, the processing target extraction unit 52, the region-of-interest specification unit 54, the support processing unit 56, the display control unit 58, and the timing detection unit 60. For example, the CPU 32 that functions as the console 30 and the GPU 34 and the storage unit 42 that function as the support processing unit 56 may be separately provided, or the GPU 34 may be provided as a so-called GPU box.

In addition, in the above-described embodiment, the aspect in which the mobile radiography apparatus having the C-arm is applied as an example of the mobile medical imaging apparatus has been described. However, the mobile medical imaging apparatus is not limited to this embodiment. For example, a combination of a mobile cart having the radiation emitting unit 10 and the radiation detector 38 which is a so-called electronic cassette may be used as the mobile medical imaging apparatus. Further, for example, a portable medical imaging apparatus that the operator carries and moves may be used. Furthermore, the imaging apparatus is not limited to the mobile medical imaging apparatus and may be a stationary medical imaging apparatus. Moreover, for example, the imaging apparatus may be a medical imaging apparatus that captures a computed tomography (CT) image, an ultrasound image, or the like.

In addition, in the above-described embodiment, for example, the following various processors can be used as a hardware structure of processing units performing various processes, such as the image acquisition unit 50, the processing target extraction unit 52, the region-of-interest specification unit 54, the support processing unit 56, the display control unit 58, and the timing detection unit 60. The various processors include, for example, a CPU which is a general-purpose processor executing software (programs) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the image processing program 43 is stored (installed) in the storage unit 42 in advance has been described. However, the present disclosure is not limited thereto. The image processing program 43 may be recorded on a recording medium, such as a compact disc read only memory (CD-ROM), a digital versatile disc read only memory (DVD-ROM), or a universal serial bus (USB) memory, and then provided. In addition, the image processing program 43 may be downloaded from an external device through a network.

What is claimed is:

1. An image processing device comprising:
   at least one processor,
   wherein the processor:
   acquires a moving image related to capture of a medical image of a subject by a medical imaging apparatus,
   extracts a frame to be subjected to a support process with a predetermined ratio that is predetermined with respect to a type of the support process, which is a diagnosis support process for supporting interpretation of the medical image or an imaging support process for supporting a positioning of the subject, from a series of frames included in the moving image, and
   executes the support process for the extracted frame.

2. The image processing device according to claim 1,
   wherein a condition for starting the support process is predetermined, and
   the processor detects a time when the support process is started on the basis of the condition and extracts a frame corresponding to the detected time as a frame, for which the support process is started, from the moving image.

3. The image processing device according to claim 2,
   wherein the processor detects the time when the support process is started using the acquired moving image.

4. The image processing device according to claim 2,
   wherein the processor detects the time when the support process is started on the basis of a movement of the subject in the moving image.

5. The image processing device according to claim 2,
   wherein the processor detects the time when the support process is started on the basis of a detection result of an ecological information detection sensor that detects ecological information of the subject.

6. The image processing device according to claim 2,
   wherein the processor detects the time when the support process is started according to a time when an instruction to execute the support process is received.

7. The image processing device according to claim 1,
   wherein the processor extracts the frame to be subjected to the support process at a regular interval from the moving image.

8. The image processing device according to claim 1,
   wherein the processor specifies a region of interest from the frame to be subjected to the support process and executes the support process for the region of interest in the frame.

9. The image processing device according to claim 8,
   wherein the medical imaging apparatus is a radiography apparatus that captures a radiographic image,
   the moving image is a fluoroscopic image, and
   the processor specifies the region of interest on the basis of an irradiation field of radiation in the radiography apparatus.

10. An image processing device comprising:
    at least one processor,
    wherein the processor extracts a frame to be subjected to a support process with a predetermined ratio that is predetermined with respect to a type of the support process, which is a diagnosis support process for supporting interpretation of the medical image or an imaging support process for supporting a positioning of the subject, from a series of frames included in a moving image related to capture of a medical image of a subject by a medical imaging apparatus, and executes the support process for the extracted frame.

11. The image processing device according to claim 1,
    wherein the medical imaging apparatus is a radiography apparatus that captures a radiographic image, and
    the moving image is a fluoroscopic image of the subject captured by the radiography apparatus.

12. The image processing device according to claim 1,
    wherein the moving image is a visible light image captured by a visible light imaging device.

13. A mobile medical imaging apparatus comprising:
    the image processing device according to claim 1; and
    a power source that supplies power to the processor of the image processing device.

14. An image processing method that is executed by a computer, the image processing method comprising:

acquiring a moving image related to capture of a medical image of a subject by a medical imaging apparatus;

extracting a frame to be subjected to a support process with a predetermined ratio that is predetermined with respect to a type of the support process, which is a diagnosis support process for supporting interpretation of the medical image or an imaging support process for supporting a positioning of the subject, from a series of frames included in the moving image; and executing the support process for the extracted frame.

15. An image processing method that is executed by a computer, the image processing method comprising:

acquiring a frame to be subjected to a support process with a predetermined ratio that is predetermined with respect to a type of the support process, which is a diagnosis support process for supporting interpretation of the medical image or an imaging support process for supporting a positioning of the subject, from a series of frames included in a moving image related to capture of a medical image of a subject by a medical imaging apparatus; and executing the support process for the extracted frame.

16. A non-transitory computer-readable storage medium storing an image processing program that causes a computer to execute a process comprising:

acquiring a moving image related to capture of a medical image of a subject by a medical imaging apparatus;

extracting a frame to be subjected to a support process with a predetermined ratio that is predetermined with respect to a type of the support process, which is a diagnosis support process for supporting interpretation of the medical image or an imaging support process for supporting a positioning of the subject, from a series of frames included in the moving image; and executing the support process for the extracted frame.

17. A non-transitory computer-readable storage medium storing an image processing program that causes a computer to execute a process comprising:

extracting a frame to be subjected to a support process with a predetermined ratio that is predetermined with respect to a type of the support process, which is a diagnosis support process for supporting interpretation of the medical image or an imaging support process for supporting a positioning of the subject, from a series of frames included in a moving image related to capture of a medical image of a subject by a medical imaging apparatus; and executing the support process for the extracted frame.

* * * * *